US010377700B2

(12) United States Patent
Battistini et al.

(10) Patent No.: US 10,377,700 B2
(45) Date of Patent: Aug. 13, 2019

(54) PROCESS FOR THE RECOVERY OF A BORONIC ACID

(71) Applicant: BRACCO IMAGING S.P.A., Milan (IT)

(72) Inventors: Elisa Battistini, Valperga (IT); Federica Buonsanti, Turin (IT); Daniela Imperio, Gattinara (IT); Luciano Lattuada, Cassina De'Pecchi (IT); Roberta Napolitano, Albiano D'Ivrea (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 15/912,772

(22) Filed: Mar. 6, 2018

(65) Prior Publication Data
US 2019/0071392 A1    Mar. 7, 2019

Related U.S. Application Data

(62) Division of application No. 15/033,737, filed as application No. PCT/EP2014/073692 on Nov. 4, 2014, now Pat. No. 9,950,991.

(30) Foreign Application Priority Data
Nov. 5, 2013 (EP) .................................... 13191551

(51) Int. Cl.
C07C 231/14     (2006.01)
C07C 231/02     (2006.01)
C07F 5/04       (2006.01)
C07F 5/05       (2006.01)
C07C 201/12     (2006.01)
C07C 227/04     (2006.01)
C07C 231/12     (2006.01)
C07F 5/02       (2006.01)
C07C 237/46     (2006.01)

(52) U.S. Cl.
CPC .......... C07C 231/14 (2013.01); C07C 201/12 (2013.01); C07C 227/04 (2013.01); C07C 231/02 (2013.01); C07C 231/12 (2013.01); C07C 237/46 (2013.01); C07F 5/025 (2013.01); C07F 5/04 (2013.01); C07F 5/05 (2013.01); Y02P 20/55 (2015.11); Y02P 20/582 (2015.11)

(58) Field of Classification Search
CPC ............... C07F 5/025; C07F 5/04; C07F 5/05
See application file for complete search history.

(56) References Cited

U.S. PATENT DOCUMENTS 5,362,905 A    11/1994   Villa et al.
5,550,287 A    8/1996    Cannata et al.

FOREIGN PATENT DOCUMENTS

| EP | 1337505 B1 | 10/2008 |
| GB | 1472050 A | 4/1977 |
| GB | 2331098 A | 5/1999 |
| JP | 2009511993 A | 3/2009 |
| RU | 2493146 C2 | 9/2013 |
| WO | 1996-037458 A1 | 11/1996 |
| WO | 1996-037459 A1 | 11/1996 |
| WO | 1996-037460 A1 | 11/1996 |
| WO | 1997-030735 A2 | 8/1997 |
| WO | 1997-047590 A2 | 12/1997 |
| WO | 1998-024757 A1 | 6/1998 |
| WO | 1998-028259 A1 | 7/1998 |
| WO | 1999-058494 A2 | 11/1999 |
| WO | 2000-029372 A1 | 5/2000 |
| WO | 2000-050385 A1 | 8/2000 |
| WO | 2002-044125 A1 | 6/2002 |
| WO | 2002-044132 A1 | 6/2002 |
| WO | 2005-019229 A1 | 3/2005 |
| WO | 2007-045011 A1 | 4/2007 |
| WO | 2009-103666 A2 | 8/2009 |
| WO | 2010-057765 A1 | 5/2010 |
| WO | 2010-121904 A1 | 10/2010 |
| WO | 2011-003894 A1 | 1/2011 |
| WO | 2011-154500 A1 | 12/2011 |

OTHER PUBLICATIONS

Office Action for Israeli application No. 245,457, dated Sep. 5, 2018 (English translation).
European Search Report for European application No. 18162482.6, dated Jul. 18, 2018.
Office Action for Japanese application No. 2016-551022, dated Jul. 3, 2018 (English translation).
Adams, Ralph W. et al., "Reversible Interactions with para-Hydrogen Enhance NMR Sensitivity by Polarization Transfer", Science, 2009, vol. 323, No. 5922, pp. 1708-1711, doi:10.1126/science.1168877, Edinburgh Research Explorer.
Bjorsvik, Hans-Rene et al., "A Selective Process for N-Alkylation in Competition with O-Alkylation: Boric Acid, Borax, and Metaborate as a Cheap and Effective Protecting Group Applicable for Industrial-Scale Synthetic Processes", Organic Process Research & Development, 2001, vol. 5, No. 5, pp. 472-478, American Chemical Society and The Royal Society of Chemistry.
Rustighi, Isabella et al., "Borate complexes of X-ray iodinated contrast agents: Characterization and sorption studies for their removal from aqueous media", Journal of Hazardous Materials 2015-206, 2012, pp. 10-16, Elsevier Ltrd.

(Continued)

Primary Examiner — Valerie Rodriguez-Garcia
(74) Attorney, Agent, or Firm — Vivicar Law, PLLC

(57) ABSTRACT

The present invention discloses a process for recovery of a boronic acid of formula $R_3$—$B(OH)_2$, wherein $R_3$ is selected from the group consisting of $C_1$-$C_6$ linear or branched alkyl, $C_3$-$C_6$ cycloalkyl, and $C_6$ aryl, optionally substituted with a group selected from the group consisting of methyl, ethyl, n-propyl, i-propyl, n-butyl, sec-butyl, t-butyl, and phenyl, comprising admixing the boronic acid with a water-immiscible organic solvent in a weight ratio between the boronic acid and the water-immiscible organic solvent from 1:10 to 1:20, adding an aqueous solution to a final pH of neutral, and partitioning the boronic acid into an organic water-immiscible phase and recovery of the organic water-immiscible phase.

7 Claims, No Drawings

(56) References Cited

OTHER PUBLICATIONS

Zhizhong, Zhao et al., "2. Phenyl boric acid cyclic esters", Protective Groups in Organic Chemistry, 1984, p. 126 (with English translation in part).
Office Action for Canadian Application No. 2,927,706, dated Apr. 7, 2017.
Office Action for Chinese Application No. 2014800605394, dated Dec. 27, 2016 (with English translation).
Office Action for Russian Application No. 2016122022, dated Dec. 22, 2017 (English translation).
European Search Report for European application No. 13191551.4, dated Apr. 3, 2014.
International Search Report and Written Opinion for PCT application No. PCT/EP2014073692, dated Jan. 19, 2005.
International Preliminary Report on Patentability for PCT application No. PCT/EP2014/073692, dated May 10, 2016.
Office Action for Canadian Application No. 3,001,399, dated May 13, 2019.

PROCESS FOR THE RECOVERY OF A BORONIC ACID

CROSS-REFERENCE TO RELATED APPLICATIONS

This application is a divisional of U.S. patent application Ser. No. 15/033,737, filed May 2, 2016, which is the national stage application of corresponding International Application Number PCT/EP2014/073692, filed Nov. 4, 2014, which claims priority to and the benefit of European Application Number EP13191551.4, filed Nov. 5, 2013, all of which are hereby incorporated by reference in their entirety.

The present invention relates to the field of organic chemistry, in particular to the synthesis of iodinated contrast agents, more in particular to the use of boron oxyacids and derivatives thereof as protecting groups. The present invention provides also compounds useful as intermediates in the above synthesis.

BACKGROUND OF THE INVENTION

Contrast agents, or contrast media, are substances that can alter the way in which a region is analyzed in medical imaging. In particular, they are able to change the contrast of an organ, an injury, or any other surrounding structure, to make visible such details that otherwise would be difficult to detect or appreciate.

Contrast agents are primarily used in the radiological or in the nuclear magnetic resonance diagnostic fields. Depending on the field of application, these derivatives present structural features, such as, in the case of molecules useful as contrast agents for X-rays analysis, the presence of one or more atom with high atomic number (e.g. iodine or barium).

Iopamidol (N,N'-bis[2-hydroxy-1-(hydroxymethyl)ethyl]-5-[(2S)(2-hydroxy-1-oxopropyl)amino]-2,4,6-triiodo-1,3-benzendicarboxamide) (II), whose structural formula is indicated below, is one of the numerous tri-iodinated diagnostic agents, commercially available and widely used for this purpose:

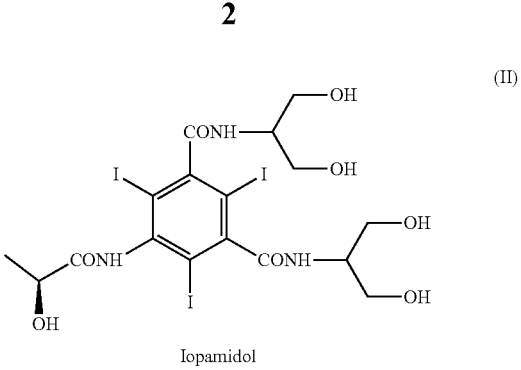

Iopamidol

The widespread use of this compound in diagnostics makes necessary for the manufacturers to dispose of easy and convenient syntheses on an industrial scale.

Iopamidol and its synthesis were first disclosed in GB1472050.

Several synthetic approaches have been since then described: they are mostly characterised by the conversion of aromatic amino derivatives into the corresponding carboxamides, by reaction with a suitable α-hydroxyacid derivative, see for instance: WO 02/44132, WO02/44125, WO 96/37459, WO 96/37460, U.S. Pat. No. 5,362,905, WO 97/47590, WO 98/24757, WO 98/28259 and WO 99/58494.

5-Amino-N,N'-bis[2-hydroxy-1-(hydroxymethyl)ethyl]-1,3-benzenedicarboxamide (V) is a key intermediate in the synthesis of Iopamidol. As shown in Scheme 1 below where prior art synthesis has been summarized, its iodination gives the intermediate 5-Amino-N,N'-bis[2-hydroxy-1-(hydroxymethyl)ethyl]-2,4,6-triiodo-1,3-benzenedicarboxamide (IV) which may be further reacted with suitable acylating agents, such as acetic anhydride in order to protect the hydroxyl groups (as described, i.e. in WO 02/44132 or in WO00/050385) and prevent their reaction with N—(S)-2-(acetyloxy)propanoyl chloride (2-acetyloxypropanoyl chloride) in the subsequent reaction. By acetylating the more reactive carboxamido-hydroxy groups, the use of an excess of 2-acetyloxypropanoyl chloride is avoided. However, the protective group, after the final deprotection with NaOH, is lost and cannot be recycled.

Scheme 1

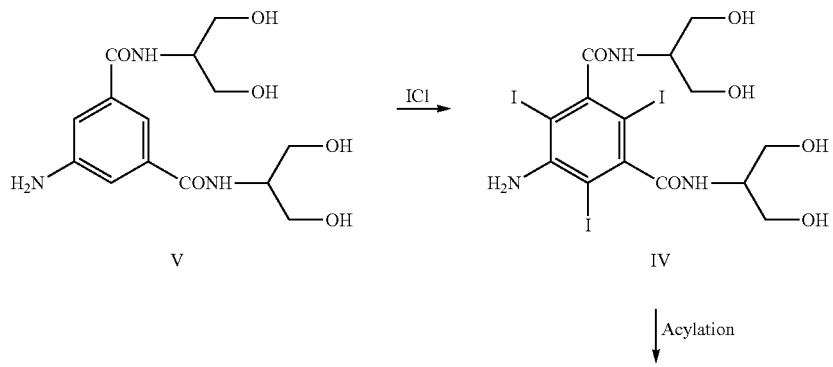

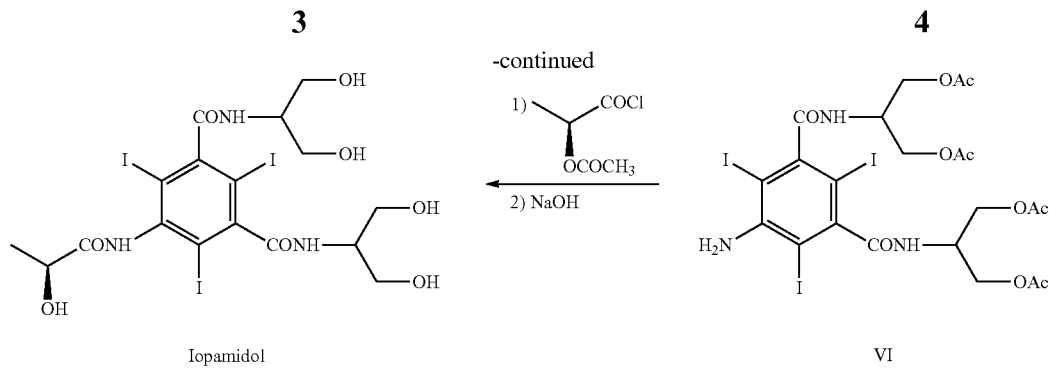

Iopamidol

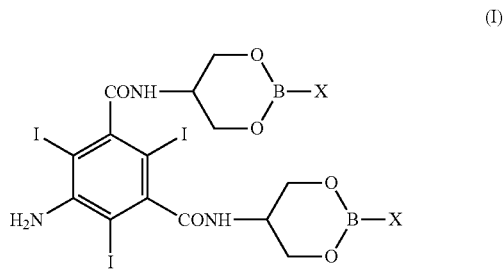

VI

Furthermore, in order to protect the hydroxyl groups, an excess of acetic anhydride is required and its presence in the mixture is incompatible in the next reaction step. Subsequently, additional precipitation and crystallization steps are required.

The main drawback of this approach is related to the isolation of the intermediate (VI), to obtain the solid in a suitable crystalline form. This procedure may lead to a loss of 10% in the yield.

There is the need of an economical synthesis of Iopamidol, in particular a synthesis allowing the recovery and recycle of the reactant used as hydroxyl protective group.

There is also the need to provide a synthesis, which, at least in the last steps, allows a one-pot series of reactions in order to avoid the isolation of intermediate compounds and to increase the overall yield.

Furthermore, reactants recovery, together with a decreased waste production and disposal represent highly desirable tasks in view of a positive final reaction balance.

Boron derivatives are known as protective agents in chemical synthesis.

GB2331098 and HR Bjørsvik, H Priebe, J Cervenka, A W Aabye, T Gulbrandsen and AC Bryde (A Selective Process for N-Alkylation in Competition with O-Alkylation: Boric Acid, Borax, and Metaborate as a Cheap and Effective Protecting Group Applicable for Industrial-Scale Synthetic Processes; Organic Process Research and Development 2001, 5, 472-478) disclose a process for N-alkylation of compounds containing 1,2 and/or 1,3 diol structures. Iodinated contrast agents are disclosed as particular embodiment. In order to avoid competing O-alkylation, this document teaches the use of boron oxyacid as diol protecting agents. Salts and esters can also be used. The reaction involving diol protection by the boron oxyacid is carried out in water. After the N-alkylation reaction has come to accomplishment, diol deprotection is carried out.

Another different use of boric oxyacids in connection with iodinated contrast media is disclosed in Journal of Hazardous Materials 205-206 (2012) 10-16 (I Rustighia, I Donatia, M Ferluga, C Campa, AE Pasqua, M Rossi, S Paoletti; Borate complexes of X-ray iodinated contrast agents: Characterization and sorption studies for their removal from aqueous media). The Authors show an effective use of boric oxyacids as a means for removing iodinated contrast media from wastewater. This adduct has a good stability at alkaline pH and is adsorbed on the ionic resin Dowex 1×4, from which it is desorbed by means of a number of desorbing agents, mainly salts.

SUMMARY OF THE INVENTION

It has now been found boron-containing protective groups which are versatile and efficiently recyclable. The new protecting boron-containing functions enable a one-pot synthesis, without intermediate isolation, allowing recovery and recycling of the protective functions and a significant increase in the overall process yields.

Moreover, these protecting groups can be recovered and recycled in the process and this represents a significant advantage in terms of cost-effectiveness of the entire process and environmental awareness.

It is an object of the present invention an intermediate Compound of formula (I)

(I)

[Structure of Compound I]

wherein X is $OR_2$ or $R_3$, and wherein $R_2$ and $R_3$ are a $C_1$-$C_6$ linear or branched alkyl, $C_3$-$C_6$ cycloalkyl, $C_6$ aryl, optionally substituted with a group selected from the group consisting of methyl, ethyl, n-propyl, i-propyl, n-butyl, sec-butyl, t-butyl and phenyl.

It is another object of the present invention a process for the preparation of Iopamidol of formula (II)

(II)

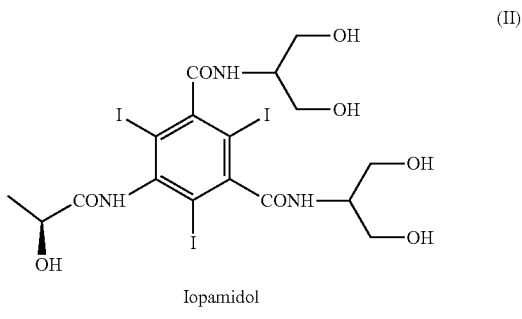

Iopamidol comprising the following reaction summarized in Scheme 2:

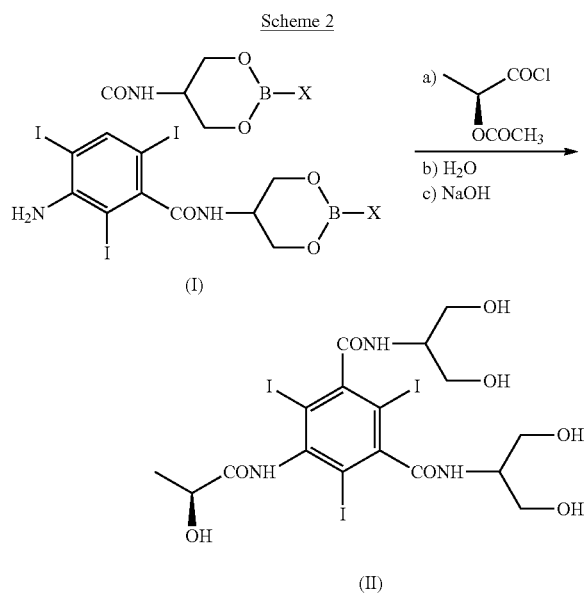

wherein the different groups are as above defined and comprising the following steps:
  a) reacting the Compound (I) with the acylating agent (S)-2-(acetyloxy)propanoyl chloride in a reaction medium to provide the N—(S)-2-(acetyloxy)propanoyl derivative of Compound (I);
  b) hydrolyzing the intermediate from step a) with an aqueous solution at a pH comprised from 0 to 7, preferably from 6 to 7 by adding water or a diluted alkaline solution such as sodium hydroxide or potassium hydroxide, freeing the hydroxyls from the boron-containing protective groups, obtaining the acetyloxy derivative of Compound (II) and optionally recovering the boron derivative;
  c) alkaline hydrolysis of the acetyloxy derivative of Compound (II) restoring the (S)-2-(hydroxy)propanoyl group to obtain Iopamidol (II).

In a first preferred embodiment, in the compound of formula (I), X is $OR_2$, wherein $R_2$ is as above defined and preferably selected from the group consisting of: ethyl, n-propyl and n-butyl.

In a second preferred embodiment, in the Compound of formula (I), X is $R_3$, wherein $R_3$ is as above defined and preferably selected from the group consisting of: butyl, isobutyl, isopentyl, n-pentyl, n-hexyl, ciclopentyl, ciclohexyl or phenyl, optionally substituted with methyl, ethyl, n-propyl, i-propyl, n-butyl, sec-butyl, t-butyl or phenyl.

In step a) of the above process, said reaction medium is an organic solvent, selected from the group consisting of N,N-dimethylformamide, N,N-dimethylacetamide, N,N-diethylacetamide, N,N-dimethylpropionamide, N-methylpyrrolidone, N-ethylpyrrolidone, tetramethylurea, N,N'-dimethylethyleneurea (DMEU), N,N'-dimethylpropyleneurea (DMPU), optionally in admixture with a water-immiscible organic solvent, herein defined co-solvent.

In step b) after the hydrolysis of the boron protective groups, recovery of the boron-derivative can be carried out by chromatography or by solvent extraction. In case chromatography is used, a suitable resin specific for boron removal can be used. For example, a suitable resin contains diolic groups and is designed to boric or boronic acid complexation and subsequent sequestration. A preferred resin is the one containing N-methyl (polyhydroxyhexyl) amine functional groups also called methylglucamine. A commercially available example of such a resin is Amberlite® IRA743. However, other resins can be selected among the commercially available ones, for example or equivalent or analogue columns, such as Duolite ES-371, Diaion CRB 02, Dowex BSR 1, Purolite S 108 and Purolite S110. Further details are provided in the Detailed Description below. Hydrolysis of boron-containing protecting groups is made by water addition.

However, recovery of the boron-derivatives is preferably carried out by solvent extraction, in particular when, according to Scheme 3 and reactant 3, R3 is butyl, phenyl or a methyl substituted phenyl (tolyl group), butyl or when a boroxine of Formula III is used and R3 has the same meaning as for reactant 3.

Overall, the process for the preparation of Iopamidol according to the present invention is presented in the following Scheme 3:

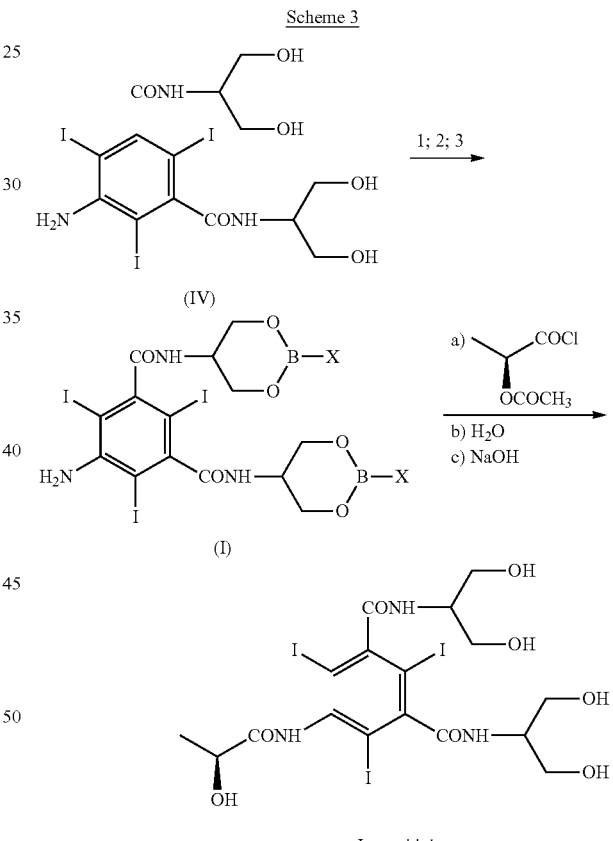

1: $B(OH)_3 + R_2OH$
2: $B(OR_2)_3$
3: $R_3B(OH)_2$
X: $OR_2$; $R_3$

In Scheme 3, which describes the synthesis of Iopamidol (II) from 5-Amino-N,N'-bis[2-hydroxy-1-(hydroxymethyl)ethyl]-2,4,6-triiodo-1,3-benzenedicarboxamide (IV), X is as defined above and in the first reaction step, the numbers 1; 2; 3, represent reactants in single, alternative embodiments. Not shown in the scheme, but part of the present invention is also the alternative reactant boroxine of Formula III.

According to the present invention, the terms "boron derivative", "boron derivatives" or "boron-containing protective group" mean the boron compounds which are used according to Scheme 3 above, with the starting Compound (IV) to give the Compound (I); as well as the compounds produced in the hydrolysis of the intermediate (I) and subsequent freeing the hydroxyls from the boron-containing protective groups. These boron derivatives can be optionally recovered in the above step c) and recycled in the process. The terms "boron derivative" or "boron derivatives" generally comprise boron oxyacids (such as boric acid and boronic acids), esters thereof and boroxine.

According to a first preferred embodiment of the present invention, and referring to Scheme 3, the intermediate Compound (I), wherein X is $OR_2$, is obtained by reacting Compound (IV) with one of a boric acid in an $R_2OH$ alcohol or a borate ester $B(OR_2)_3$, wherein $R_2$ is as above defined.

According to a second preferred embodiment of the present invention, and also referring to Scheme 3, the intermediate Compound (I), wherein X is $R_3$ is obtained by reacting the Compound (IV) with a boronic acid $R_3$—$B(OH)_2$, wherein $R_3$ is as above defined. Alternatively, this second preferred embodiment, not shown in Scheme 3, but part of the present invention is achieved by reacting the Compound (IV) with a boroxine of formula (III):

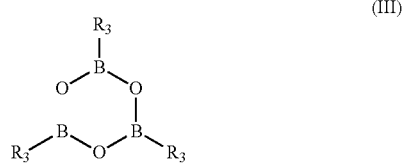

(III)

wherein $R_3$ is as above defined.

In one embodiment of the present invention, said process for the preparation of Iopamidol (II) comprises:

x) reacting the Compound of formula (IV) with a boric acid ester $B(OR_2)_3$, wherein $R_2$ is as above defined (see Scheme 3 above, reactant 2) to provide the intermediate of formula (I) above disclosed;

a) treating said intermediate Compound (I) with (S)-2-(acetyloxy)propanoyl chloride to obtain N—(S)-2-(acetyloxy)propanoyl derivative of Compound (I)

b) releasing boric acid; and c) restoring the (S)-2-(hydroxy)propanoyl group to obtain Iopamidol (II) by alkaline hydrolysis.

In said process, the boric acid ester can be restored for subsequent use. In this connection, the boric acid, obtained in the final step, is recovered, reacted with an $R_2$—OH alcohol, wherein $R_2$ is as above defined, and recycled in a new process.

In an embodiment of the recovery step, said boric acid is treated with a suitable resin, such as a resin specific for boric acid, for example the commercially available Amberlite™ IRA743, being intended that the person skilled in the art can select the proper way to recover boric acid by resorting to the general common knowledge in this matter.

In another embodiment of the present invention, said process for the preparation of Iopamidol (II) comprises:

x') reacting the Compound (IV) with boric acid with an alcohol $R_2OH$, wherein $R_2$ is as above defined (see Scheme 3 above, reactant 1) to provide the intermediate of formula (I) above disclosed;

a) treating said intermediate (I) with (S)-2-(acetyloxy)propanoyl chloride to obtain N—(S)-2-(acetyloxy)propanoyl derivative of Compound (I), b) releasing boric acid; and c) restoring the (S)-2-(hydroxy)propanoyl group to obtain Iopamidol (II) by alkaline hydrolysis.

In said process, the boric acid and the alcohol form the corresponding boric acid ester in situ, and the process can be carried out as in the case explained above using the boric acid ester. The boric acid ester is then restored for subsequent use as shown above.

The process can be carried out in batch mode, or, conveniently, in continuous mode.

In another embodiment of the present invention, in the Compound of formula (I) X is $R_3$, as above defined and is preferably a phenyl, a methyl substituted phenyl, a methyl or a butyl group.

According to this embodiment, an exemplary process for the preparation of Iopamidol (II) is illustrated in the above Scheme 3, reactant 3.

Said Process Comprises:

x") reacting the Compound of formula (IV) with a boronic acid $R_3$—$B(OH)_2$ or a boroxine (III) wherein $R_3$ is as above defined, and is preferably selected from a phenyl, a methyl substituted phenyl, methyl and butyl to provide the intermediate of formula (I);

a) treating said intermediate (I) with (S)-2-(acetyloxy)propanoyl chloride to obtain the acetyloxy derivative of Compound (I), b) releasing boronic acid;

c) restoring the (S)-2-(hydroxy)propanoyl group to obtain Iopamidol (II) by alkaline hydrolysis.

In said process the boronic acid can be recovered for subsequent use. In this connection, the boronic acid, obtained in the final step, is recovered with two possible approaches: by extracting with an organic water-immiscible solvent, for example 4-methyl-2-pentanone, 2-pentanone, 3-pentanone, dibutyl ether, 2-methyl-tetrahydrofurane, ciclopentylmethyl ether, methyl isopropyl ketone, methyl isopentyl ketone, ethyl acetate, butyl acetate, pentyl acetate, isopentyl acetate, isopropyl acetate, removing the solvent and recycling the recovered boronic acid in the process, or alternatively, as described above for boric or boronic acid complexation, i.e. by treating the final reaction mixture with a resin suitable for boron removal, such as those mentioned in step c) above, among which, for example, an Amberlite® IRA 743.

The recovery process can be carried out in a batch mode, or, more conveniently, in a continuous mode. In a preferred embodiment, phenylboronic, p-tolyl boronic or n-butylboronic acids are used and recycled.

In another embodiment, in the Compound of formula (I), X is $R_3$, as above defined, preferably phenyl, a methyl substituted phenyl, methyl or butyl. More preferably in Compound of formula (I) $R_3$ is phenyl.

The preparation of compound of formula (I) as an intermediate in the preparation of Iopamidol (II) can also be carried out as disclosed in the previous embodiment, but using a boroxine of formula (III) is used instead of the boronic acid. Triphenylboroxine and trimethylboroxine are preferred boroxines and $R_3$ in compound (I) is preferably phenyl or methyl. According to this embodiment, phenylboronic acid or methylboronic acid are released upon hydrolysis of the hydroxyl groups, freed from the boron-containing protective moiety and the boronic acids can be restored for subsequent use, as disclosed above.

Compound (I) can be isolated and characterized as will be described more in details below. Accordingly, compound of formula (I) represents a further object of the present invention as well as its use as intermediate in the synthesis of Iopamidol (II).

After the OH protection is completed, which is preferably achieved by water distillation, an acetylation step is carried out on Compound (I) preferably in a solvent selected from the group consisting of: N,N-dimethylformamide, N,N-dimethylacetamide (DMAC), N,N-diethylacetamide, N,N-dimethylpropionamide, 1-methyl-2-pyrrolidone, 1-ethyl-2-pyrrolidone, tetramethylurea, N,N'-dimethylethyleneurea (DMEU), N,N'-dimethylpropyleneurea (DMPU). Preferably N,N-dimethylacetamide is used and more preferably, N,N-dimethylacetamide has a very low water content or is anhydrous. The solvent may also comprise a co-solvent which is an organic solvent immiscible in water, selected among: 4-methyl-2-pentanone, 2-pentanone, 3-pentanone, dibutyl ether, 2-methyl-tetrahydrofurane, ciclopentylmethyl ether, methyl isopropyl ketone, methyl isopentyl ketone, ethyl acetate, butyl acetate, pentyl acetate, isopentyl acetate, isopropyl acetate. A preferred solvent/co-solvent mixture is represented by DMAC and 4-methyl-2-pentanone, 3-pentanone or 2-pentanone.

The presence of a co-solvent in step a) is particularly preferred when the boron protective groups have to be recovered at a later time by co-solvent extraction.

In another embodiment of the present invention, the process can be carried out starting from a suitable Compound (V).

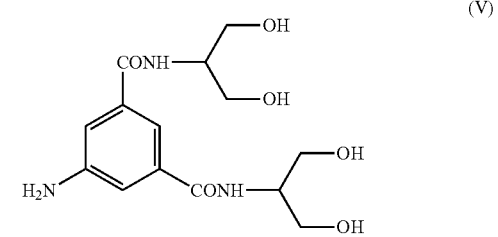

(V)

According to this embodiment, an object of the present invention is a process according to the following Scheme 4:

Scheme 4

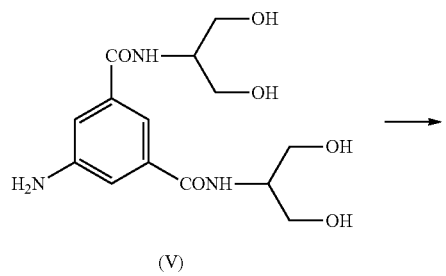

(V)

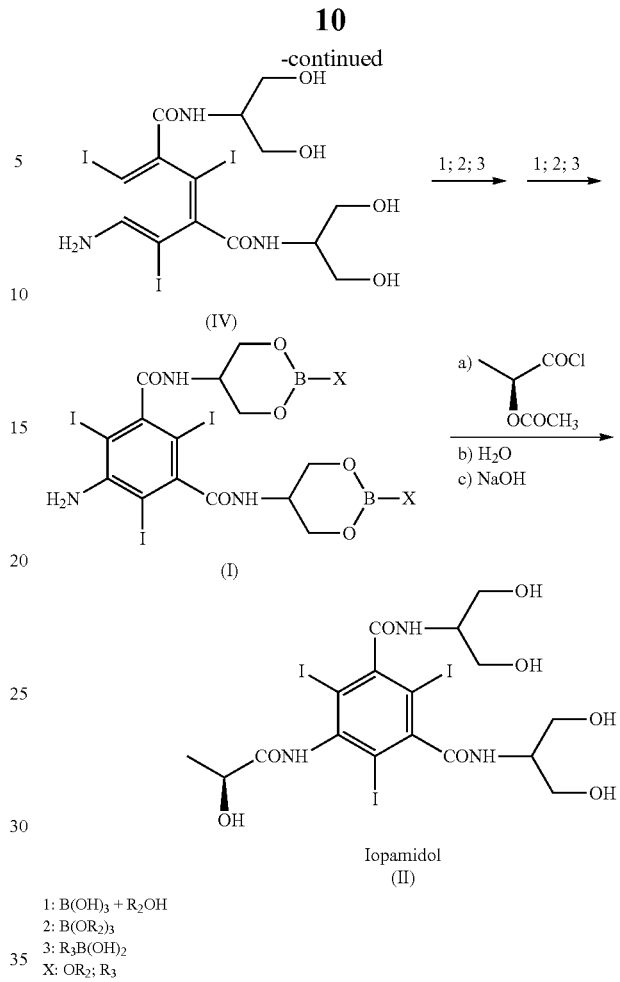

(IV)

(I)

Iopamidol
(II)

1: $B(OH)_3 + R_2OH$
2: $B(OR_2)_3$
3: $R_3B(OH)_2$
X: $OR_2$; $R_3$

Scheme 4 describes the synthesis of Iopamidol (II) from 5-Amino-N,N'-bis[2-hydroxy-1-(hydroxymethyl)ethyl]-1,3-benzenedicarboxamide (V); X is as defined above and in the first reaction step the numbers 1; 2; 3 represent reactants in single, alternative embodiments. Not shown in the scheme, but part of the present invention is also the alternative reactant boroxine.

The Compound (V) can also be prepared as described in WO02/44125 or WO00/029372.

The iodination of the aromatic ring is also carried out according to methods disclosed in the numerous literature on Iopamidol synthesis, e.g. in WO96/037458, WO2009/103666, WO2010/121904, WO2011/154500 and WO2011/003894.

In a particular aspect, and object of the present invention, Compound (V) is prepared according to the following Scheme 5:

Scheme 5

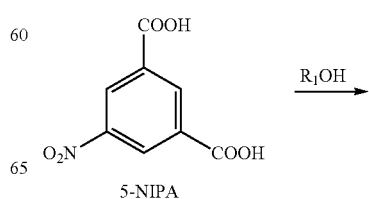

5-NIPA

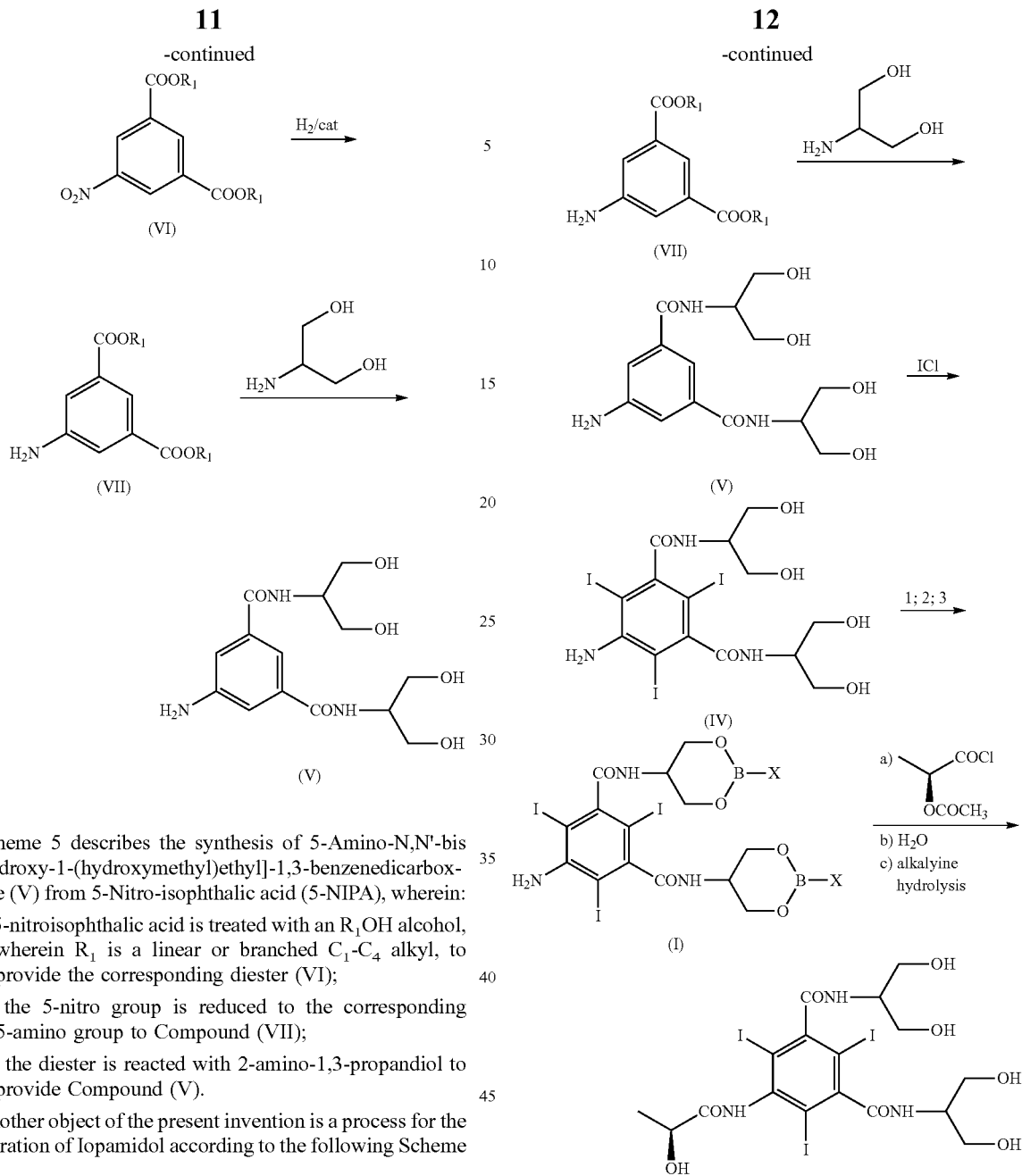

Scheme 5 describes the synthesis of 5-Amino-N,N'-bis[2-hydroxy-1-(hydroxymethyl)ethyl]-1,3-benzenedicarbox-amide (V) from 5-Nitro-isophthalic acid (5-NIPA), wherein:
i) 5-nitroisophthalic acid is treated with an $R_1OH$ alcohol, wherein $R_1$ is a linear or branched $C_1$-$C_4$ alkyl, to provide the corresponding diester (VI);
ii) the 5-nitro group is reduced to the corresponding 5-amino group to Compound (VII);
iii) the diester is reacted with 2-amino-1,3-propandiol to provide Compound (V).

Another object of the present invention is a process for the preparation of Iopamidol according to the following Scheme 6:

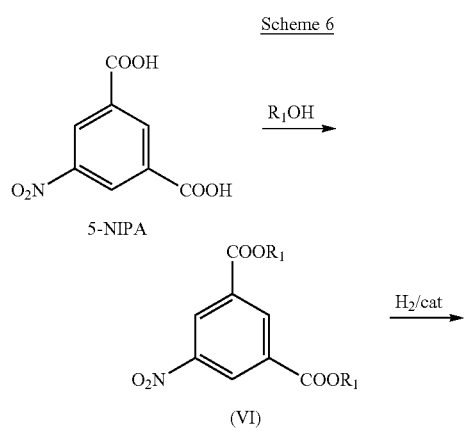

Scheme 6 describes the synthesis of Iopamidol (II) from 5-Nitro-isophthalic acid, wherein:
i) 5-nitroisophthalic acid is treated with an $R_1OH$ alcohol, wherein $R_1$ is a linear or branched $C_1$-$C_4$ alkyl, preferably butyl, to provide the diester (VI);
ii) the 5-nitro group is reduced to provide the Compound (VII);
iii) the diester is reacted with 2-amino-1,3-propandiol to provide the Compound (V);
iv) the Compound (V) is iodinated at positions 2,4,6, to provide the Compound (IV);

v) the Compound (IV) is treated with boric acid or a derivative thereof according to the present invention, to provide the Compound of formula (I) according to the present invention;

vi) the Compound of formula (I) is finally transformed into Iopamidol (II) as described above.

The above objects of the present invention and other embodiments will be now disclosed in detail in the following description.

DETAILED DESCRIPTION OF THE INVENTION

The present invention discloses a process for the preparation of Iopamidol (II) comprising the following reaction:

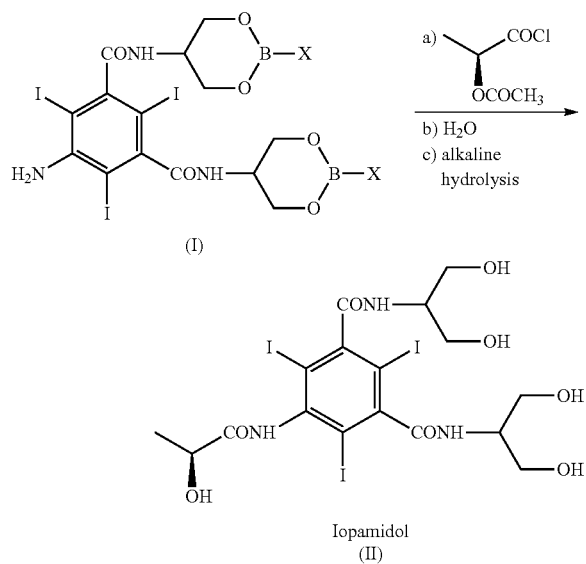

wherein X is $OR_2$ or $R_3$, and wherein $R_2$ and $R_3$ are a $C_1$-$C_6$ linear or branched alkyl, $C_3$-$C_6$ cycloalkyl, $C_6$ aryl, optionally substituted with a group selected from the group consisting of methyl, ethyl, n-propyl, i-propyl, n-butyl, sec-butyl, t-butyl and phenyl, more preferably phenyl, a methyl substituted phenyl, methyl and butyl,
and comprising the following steps:
  a) reacting the Compound (I) with the acylating agent (S)-2-(acetyloxy)propanoyl chloride in a reaction medium to provide the N—(S)-2-(acetyloxy)propanoyl derivative of Compound (I);
  b) hydrolyzing the intermediate from step a) with an aqueous solution at a pH comprised from 0 to 7, preferably from 6 to 7 by adding water or a diluted alkaline solution such as sodium hydroxide or potassium hydroxide, freeing the hydroxyls from the boron-containing protective groups, obtaining the acetyloxy derivative of Compound (II) and optional recovery of the boron derivative;
  c) alkaline hydrolysis of the acetyloxy derivative of Compound (II) restoring the (S)-2-(hydroxy)propanoyl group to obtain Iopamidol (II).

According to step a) the reaction medium is preferably a reaction medium having the minimum water content compatible with the reaction, more preferably, an anhydrous reaction medium.

The reaction medium is conveniently selected by the person of ordinary skill in the art, based on the common knowledge for this kind of reaction. The medium is typically an organic solvent capable of dissolving the Compound of formula (I) and not interfering with the acylating reagent (S)-2-(acetyloxy)propanoyl chloride. Preferred examples of organic solvent usable in this step are inert dipolar aprotic solvents, such as for example N,N-dimethylformamide, N,N-dimethylacetamide, N,N-diethylacetamide, N,N-dimethylpropionamide, 1-methyl-2-pyrrolidone, 1-ethyl-2-pyrrolidone, tetramethylurea, N,N'-dimethylethyleneurea (DMEU), N,N'-dimethylpropyleneurea (DMPU).

N,N-Dimethylacetamide (DMAC), with a low water content or anhydrous, is the preferred one. The organic solvent used in this step can be also in admixture with a co-solvent. Preferred co-solvents are selected among those organic and immiscibile in water, such as: 4-methyl-2-pentanone, 2-pentanone, 3-pentanone, dibutyl ether, 2-methyl-tetrahydrofurane, ciclopentylmethyl ether, methyl isopropyl ketone, methyl isopentyl ketone, ethyl acetate, butyl acetate, pentyl acetate, isopentyl acetate, isopropyl acetate. A preferred solvent/co-solvent mixture is represented by DMAC and 4-methyl-2-pentanone, 3-pentanone or 2-pentanone.

In step a) the stoichiometric ratio between the Compound of formula (I) and the chiral acylating agent (S)-2-(acetyloxy)propanoyl chloride is the one usually employed in the synthesis of Iopamidol (see for example GB1472050 Example 1b). A stoichiometric excess is preferred depending on the reaction conditions.

Humidity should be kept controlled in the reaction environment, therefore, it is preferred to carry out the reaction in an inert atmosphere, for example dry nitrogen or argon.

The reaction temperature is typically around room temperature, even though higher or lower temperatures can be used compatibly with the stability of the reactants and the final product.

The reaction is carried out for a time spanning from few minutes to few days, typically from 8 to 30 hours, more conveniently from 12 to 30 hours, for example for 18 hours. Reaction time depends on the reaction conditions: the solvent used, reactants ratio and purity, temperature. The person of ordinary skill in the art can find the optimal conditions by recurring to his personal knowledge and experience.

The completion of the reaction can be detected by ordinary analytical means used in organic chemistry, for example spectrometric equipment, such as $^1$H-NMR, IR; chromatographic equipment, for example TLC, HPLC, GLC.

To this purpose, and with reference to Scheme 2, the reaction mixture resulting from step a) of the process of the present invention is transferred into an aqueous medium (step b). Conveniently, water (or a diluted alkaline solution, such as a NaOH or a KOH solution) is added in the same reaction vessel where acylation step a) has been performed. Transfer of the organic phase into a different vessel containing water can also be done. Normally, the amount of water volume or weight is at least the same of the organic phase, preferably higher, for example 2-3 times the volume of the organic phase, compatibly with the subsequent operations and not exceeding in dilution. Acetyl Iopamidol protected hydroxyl groups are then freed from the boron-containing protecting groups by hydrolysis, adding water or diluted alkaline solutions, such as diluted NaOH or KOH to the acidic reaction mixture. The recovery of the boron-containing protective groups after their hydrolysis on the acetyloxy derivative of Compound of Formula (I) in step b) can be performed by treating the reaction mixture with an ion exchange resin, typically an anionic exchange one, preferably one specific for boron sequestration, such as a resin with diolic functions, more preferably with functions selected in the group consisting of: methylglucamine, diethanolaminomethyl preferably on a polystyrene matrix, glycidyl preferably on a methacrylate matrix, iminodipropylene glycol, amino-bis(propane cis 2,3 diol), hydroxyethylamino propylene glycol. Some resins, such as those with methylglucamine functions are also commercially available and can be selected from manufacturers' catalogues, for example Resindion of Mitsubishi Chemical, Dow Chemical, etc. Typical example is Duolite ES-371, preferred example is Amberlite™ IRA743 by Dow Chemical Company or other suppliers. This embodiment applies preferably to boric acid derivatives: conveniently, the resin is loaded into a column and the phase is eluted through it.

Alternatively and according to the preferred embodiment described below when a boronic acid such as phenylboronic, p-tolylboronic or butylboronic acid or a boroxine (such as phenylboroxine or methylboroxine) are used as the boron-containing protective groups, the recovery of boron-containing protective groups is carried out by extraction with an organic solvent immiscibile in water selected from the group consisting of: 4-methyl-2-pentanone, 3-pentanone, 2-pentanone, dibutyl ether, 2-methyl-tetrahydrofurane, ciclopentylmethyl ether, methyl isopropyl ketone, methyl isopentyl ketone, ethyl acetate, butyl acetate, pentyl acetate, isopentyl acetate, isopropyl acetate. Preferred extraction solvents are 4-methyl-2-pentanone (MIBK), 3-pentanone or 2-pentanone.

According to this embodiment and to Scheme 3, Compound I is preferably prepared directly in a polar solvent in admixture with the water-immiscible organic solvent (co-solvent) useful for boron-containing protective groups extraction as described below. A preferred solvent/co-solvent mixture is represented by DMAC and 4-methyl-2-pentanone (MIBK), 3-pentanone or 2-pentanone (i.e. in a ratio comprised from 1:10 to 1:4 weight/weight).

The boronic acid or boroxine are added in a slight molar excess compared to the triiodobenzenecarboxamide (Compound IV). The suspension is admixed and heated to 90-95° C. and water is preferably distilled off to complete the protection reaction. Formation of Compound I can be assessed i.e. by $^1$H-NMR.

According to a particularly preferred embodiment, steps a)-c) can then be carried out in a single pot, for example as follows: (S)-2-(acetyloxy) propanoyl-chloride is added to the mixture under nitrogen atmosphere and stirred for a few hours, to achieve the acetyloxy propanoyl derivative of Compound I. Release of the boron protecting groups by hydrolysis of the acetyloxy propanoyl derivative of Compound I is usually obtained with (water or) a diluted alkaline solution, to neutral pH (i.e. comprised from 5-8), preferably comprised from 6-7 which allows for a good selectivity in the further recovery of the boron protective group with the water-immiscible solvent.

The recovery of the boron protective group, which is usually quantitative, can be carried out in batch or in a continuous mode. In both procedures the amount of organic water immiscible solvent is maintained in a ratio with the boronic acid compound comprised from 1:10 to 1:20, preferably from 1:13 to 1:16 more preferably about 1:15. In the batch procedure this amount can be added in one or more aliquots.

The so obtained biphasic mixture comprises an aqueous phase with the acetyl-Iopamidol, which is recovered for purification, followed by hydrolysis of the acetyl group to achieve Iopamidol, while the the boronic acid is partitioned in the organic phase which is recovered, optionally preferably distilled to concentrate the boron-protective containing groups and recycled.

Recycling of the boronic acid solution can be accomplished after addition of the reaction solvent of choice, i.e. DMAC (5-10% of the organic solution) and co-solvent distillation, preferably under vacuum and at a temperature below 40° C. to achieve a boronic acid concentration of about 10%. The recycled solution can then be used indefinitely preferably by addition of a small quantity (i.e. corresponding to 5-20% of recycled boronic acid present in the organic solution) of fresh boronic acid.

As the next step, either the aqueous solution eluted from the column specific for sequestering the boronic acid, or alternatively coming from the extraction by means of an organic solvent, and comprising N,N'-bis[2-hydroxy-1-(hydroxymethyl)ethyl]-5-[(2S)(2-acetoxy-1-oxopropyl)amino]-2,4,6-triiodo-1,3-benzendicarboxamide, also known as acetyl-Iopamidol is then de-salted from organic and inorganic salts by means of ion exchange resins.

In step c) the neutral solution obtained is loaded onto a strong anionic resin, preferably a resin with trimethylamine functional groups bound to a polymeric matrix material such as Relite® 3ASFB, to release raw Iopamidol, essentially as described in U.S. Pat. No. 5,550,287 with the exception that Iopamidol is released with a diluted aqueous solution of a strong acid, such as HCl, H$_2$SO$_4$, being hydrochloric acid preferred. Alternatively, Iopamidol release can be effected in batch, in basic conditions, as disclosed e.g in WO97/30735, Example 1, i.e. by treating the acetyl Iopamidol containing mix in strongly alkaline pH conditions followed by salt removal, preferably by chromatography onto ionic exchange resins, preferably at first onto a strongly cationic resin followed by a weak anionic resin.

Hydrolysis of acetyl-Iopamidol onto a strong anionic resin, is more efficient and is therefore preferred. According to this embodiment, the process is made simpler because the purification and hydrolysis are, in practice, carried out in a single step.

The product is further purified in a conventional manner, for example as described in more details in the Experimental Part by crystallization with 2-butanol-water to a pharmaceutical grade according to the national or European Pharmacopoeias.

The boric acid or the derivative thereof used in the above embodiments of the process are recovered as described above and are preferably recycled in the process.

The novel Compound of formula (I) can be prepared according to the different embodiments. For example starting from Compound (IV) as detailed below, or other synthetic pathways disclosed herein. Although in the process for the preparation of Iopamidol (II) Compound (I) is not necessarily isolated, it can be isolated, for example after reaction with Compound (IV), as shown in the above Scheme 3 for characterization purposes, i.e by $^1$H-NMR. Isolation of Compound (I) can be done according to conventional work-up methods, well known in the art, such as for example, extraction, precipitation, chromatographic separation. One exemplary way to characterize the Compound (I) is dissolving it in a suitable solvent, for example dimethylacetamide, adding a precipitation solvent, for example toluene and isolating the formed precipitate. Conveniently, the precipitate can be redissolved, for example heating the precipitation solution, and subsequent cooling. The obtained white solid is isolated, for example by filtration. The analytical characterization can be done according to well-known methods, for example elementary analysis, melting point, spectroscopy (such as NMR, IR) as better detailed in the Experimental Part.

In another aspect of the present invention, Iopamidol (II) is prepared by starting from the above Compound of formula (IV).

This Compound is a well-known intermediate, as it is its preparation, in the prior art syntheses of Iopamidol (II), see for example WO0244125 and the references cited therein.

According to the present invention, this Compound (IV) is treated with boric acid or a derivative thereof to provide the Compound of formula (I), as disclosed above.

Boric acid and its derivatives used in the present invention are well-known compounds which are commercially available or can be prepared according to literature methods. For example, boric acid esters $B(OR_2)_3$, wherein $R_2$ is as above defined, boronic acids $R_3$—$B(OH)_2$, and boroxine of formula (III)

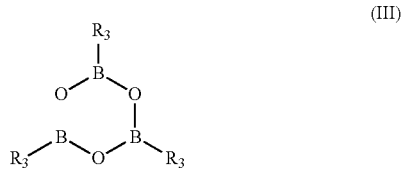
(III)

wherein $R_3$ has the same meaning and preferred embodiments as above defined, are described together with their preparation in the general literature, such as for example Ullmann's Encyclopedia of Industrial Chemistry, VCH, last edition; Dennis G. Hall (ed.) Boronic Acids, Wiley VCH, last ed.; March's Advanced Organic Chemistry, Wiley, last ed.; Kirk Othmer Encyclopedia of Chemical Technology, Wiley, last ed.; Lawrence Barton et al. (eds.) Boron Compounds, Springer Verlag, 1977.

Just for sake of exemplification, boric acid esters are prepared according to the general reaction:

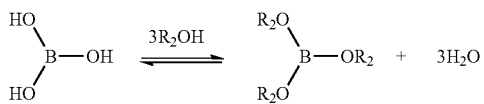

wherein $R_2$ is as above defined.

In one embodiment of the present invention, the Compound (IV) is treated with boric acid and an $R_2OH$ alcohol in a reaction medium. The reaction medium is a solvent compatible with reaction conditions, reactants and final product. Conveniently, the reaction medium is the same organic solvent used in the reaction from Compound (I) to Iopamidol (II) (step a) (see Scheme 2). In a preferred embodiment, N,N-dimethylacetamide is the solvent. The reaction is carried out at a temperature comprised from 60° C. to 100° C. or higher, for a time sufficient to completion. Check of completion of reaction, i.e. until the water content is at minimum or very low, for example <0.5%, is done by conventional methods, for example by $^1$H-NMR or by water content determination in the reaction mix, i.e. by the Karl Fischer titration. The obtained Compound (I) can be isolated or directly treated with the chiral acylating agent (S)-2-(acetyloxy)propanoyl chloride in the same reaction solvent, thus achieving a "one-pot" process. The person skilled in the art knows the meaning of the term "one-pot" process and no further explanations are necessary.

In another embodiment of the present invention, the Compound (IV) is directly treated with a boric acid ester $B(OR_2)_3$ in a reaction medium. The reaction can be carried out as for the above embodiment of boric acid and alcohol. Compound (I) can be either isolated for subsequent reaction or used in "one-pot" process.

Preferred borates are selected from the group consisting of t-butyl-, n-propyl and ethyl borate. Esters with different alkyl groups can also be used. The reaction can be carried out as for the above embodiment of boric acid and alcohol. Compound (I) can be either isolated for subsequent reaction or used in "one-pot" process.

In another embodiment of the present invention, the Compound (IV) is treated with a boronic acid anhydride, or boroxine of formula (III) above. Preferred boroxines are tri(phenyl)boroxine and tri(methyl)boroxine. The reaction can be carried out as for the above embodiment of boronic acid. Compound (I) can be either isolated for subsequent reaction or used in "one-pot" process.

In a preferred embodiment, the reaction between the Compound (IV) and the boric acid or its derivative, is carried out for a certain time and before shifting to the next step of N-acylation to Iopamidol (II), it is advisable to remove part of the solvent, for example by distillation, even better by vacuum-distillation, in order to control water content, preferably until the water content is at minimum or at least very low, for example <0.5% (determined by Karl Fischer titration).

Of note the diol protection approach by the boron derivatives used according to the present invention can be used also for the preparation of other iodinated X-ray contrast agents, beside Iopamidol such as for example Iomeprol, Iodixanol, Ioversol, Iohexol, Iopromide, etc.

In another aspect, the present invention provides a process for the preparation of Iopamidol (II) as shown in the above Scheme 4. 5-amino-N,N'-bis[2-hydroxy-1-(hydroxymethy)ethyl]-1,3-benzenedicarboxamide (Compound (V)) is a well-known compound and one of its preparations is disclosed for example in WO0244125. According to the present invention, this Compound is subjected to iodination of the benzene ring with a method known in the art, for example as disclosed in the same WO0244125 and references cited therein, to obtain 5-amino-N,N'-bis[2-hydroxy-1-(hydroxymethy)ethyl]-2,4,6-triiodo-1,3-benzenedicarboxamide (Compound (IV)).

In another aspect, the present invention provides a process for the preparation of Iopamidol (II) as shown in the above Scheme 5. Starting from 5-nitro-1,3-benzenedicarboxylic acid (5-nitroisophthalic acid or 5-NIPA), 5-amino-N,N'-bis[2-hydroxy-1-(hydroxymethy)ethyl]-1,3-benzenedicarboxamide (V) is prepared, for example as disclosed in WO0244125 and WO0029372.

According to the present invention, this Compound (V) is subjected to iodination of the benzene ring as above mentioned to obtain 5-amino-N,N'-bis[2-hydroxy-1-(hydroxymethy)ethyl]-2,4,6-triiodo-1,3-benzenedicarboxamide (Compound (IV)).

Compound (IV) is then processed according to the present invention to Iopamidol (II) through the intermediate (I).

Advantageously, a "one-pot" process can be performed.

The preferred synthetic pathway to Compound (V) is described in the Scheme 6 below, shown for one exemplary embodiment:

Scheme 6

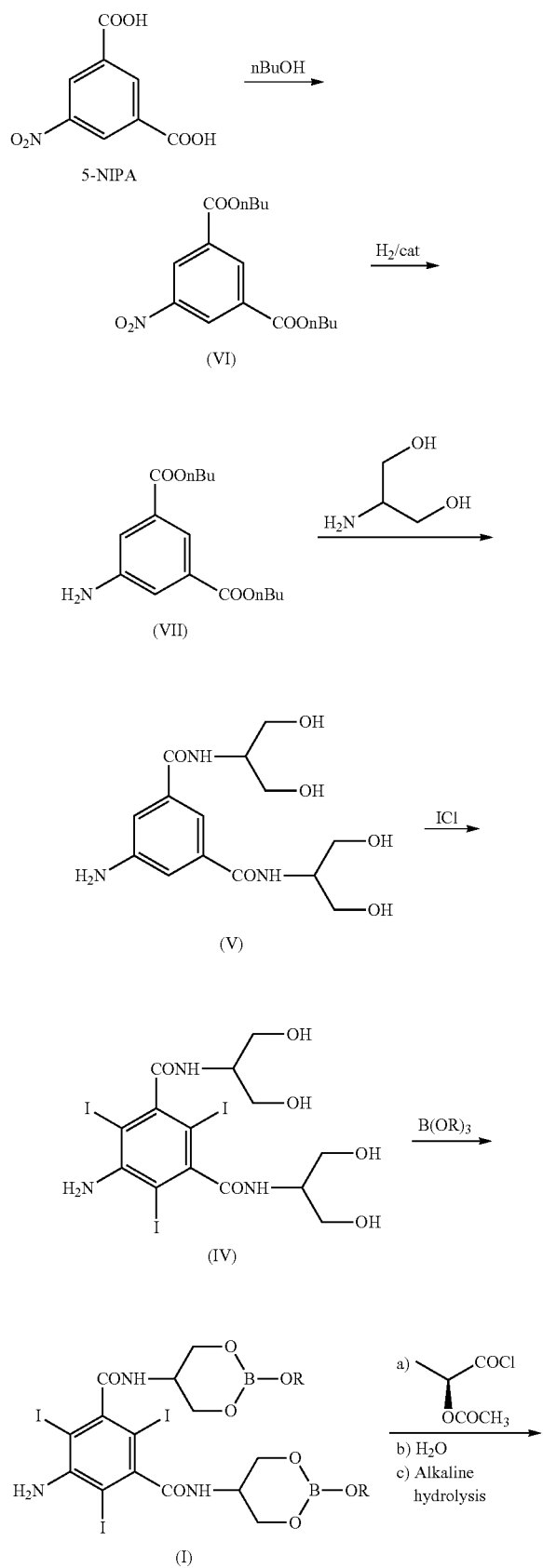

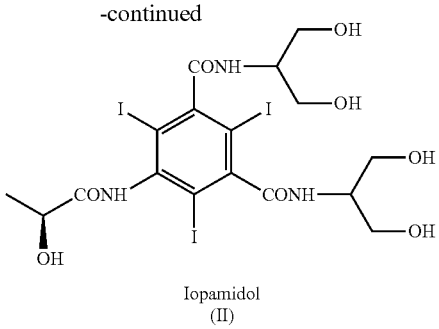

Iopamidol
(II)

The scheme 6 represents the synthetic pathway to Iopamidol (II) from 5-NIPA according to an exemplary embodiment.

The first part of the synthesis, from NIPA to Compound (V), is a "one-pot" synthesis, without intermediate isolation. It consists of three steps (esterification, hydrogenation, amidation), carried out in a convenient solvent, for example n-butanol in case a n-butyl ester is preferred. The esterification is performed in presence of a well-known esterification catalyst, for example an acid catalyst such as para-toluensulfonic acid, methansulfonic acid, sulfuric acid, preferably methanesulfonic acid. Subsequently, the hydrogenation is carried out as known by the skilled man, for example as described in EP1337505 and preferably by catalytic hydrogenation in presence of 5% Pd/C or other equivalent catalyst. In this case, after catalyst removal, the mixture is concentrated for the next amidation step, which is carried out essentially by two alternative methods:

Amidation neat, without solvent and with a consistent excess of serinol, that is recovered by an anionic resin and recycled in the reaction. Compound (V) is not isolated, but directly transferred to a new reactor vessel for the iodination step.

Amidation in the presence of an organic solvent and a co-solvent as described in EP1337505 preferably in methanol, in presence of a basic catalyst. During the reaction a precipitation occurs and the obtained Compound (V) is filtered off. The solid is directly redissolved in water and transferred to the next reactor vessel for the iodination step.

A preferred embodiment is represented by the amidation in the presence of an organic solvent and a co-solvent.

The iodination reaction is performed on an aqueous solution containing Compound (V), synthesized following one of the two approaches mentioned above. The iodination procedure is done according to well-known methods, see above for related references, to give the intermediate (IV). Then the process proceeds as disclosed above according to steps a)-c).

According to a further embodiment, the invention refers to a process for the recovery of boronic acids from a reaction mixture where these are used as diol protecting groups. This allows their re-use for the same purpose in a new synthesis. Even though this recovery and recycling is preferably carried out in the process for the preparation of Iopamidol according to the present invention and as described above, the recovery represents a more general embodiment for boronic acids recycling, because it provides quantitative yields (usually >90%, preferably >95% and more preferably at least 99%) of these generally expensive reagents, thus representing a great economic advantage for large scale industrialization.

An even greater advantage can be foreseen when this process is carried out in a continuous mode and in industrial processes where recovery and recycling can be optimized.

According to this embodiment, the aqueous reaction mixture obtained after hydrolysis of the diol protective groups, which comprises the boronic acid used for diol protection or in which a boronic acid is formed after hydrolysis (for example when a boroxine of Formula III is used for diol protection) and which optionally comprises a polar solvent such as: N,N-dimethylformamide, N,N-dimethylacetamide (DMAC), N,N-diethylacetamide, N,N-dimethylpropionamide, N-methylpyrrolidone, N-ethylpyrrolidone, tetramethylurea, N,N'-dimethylethyleneurea (DMEU), N,N'-dimethylpropyleneurea (DMPU) is added with an organic water-immiscible solvent.

The organic water-immiscible solvent is selected among: 4-methyl-2-pentanone (MIBK), 3-pentanone, 2-pentanone, dibutyl ether, 2-methyl-tetrahydrofurane, ciclopentylmethyl ether, methyl isopropyl ketone, methyl isopentyl ketone ethyl acetate, butyl acetate, pentyl acetate, isopentyl acetate, isopropyl acetate.

A preferred ratio between the boronic acid and the water-immiscibile solvent (the boronic acid extraction solvent) is comprised from 1:10-1:20 (w/w) more preferably comprised from 1:13-1:16 and even more preferably about 1:15.

The boronic acid used as the boron-containing diol protective group, recovered according to this embodiment, is preferably phenylboronic, p-tolyl boronic or butyl boronic acid, or when phenylboroxine or methylboroxine are used for diol protection, phenylboronic acid or methyl boronic acid can be recovered upon hydrolysis.

The water immiscibile organic solvent can be further re-extracted with an aliquot of an aqueous solution with a pH comprised from 0-7, or preferably close to neutrality at a pH comprised from 6 to 7 when the recovery is carried out after hydrolysis of Compound I and according to the present invention to improve the selectivity of boronic acid recovery.

Partitioning of the boronic acid into the organic phase for its recovery can be achieved either in batch or in a continuous mode, by optimization methods known to the skilled man.

The following examples further illustrate the invention in more details.

Example 1: Preparation of Iopamidol (II) Starting from Compound (IV) and Using a Boronic Acid With reference to Scheme 3, 5-Amino-N,N'-bis[2-hydroxy-1-(hydroxymethyl)ethyl]-2,4,6-triiodo-1,3-benzenecarboxamide (IV) (1 kg; 1.42 mol) and phenylboronic acid (X=Ph) (363 g; 2.98 mol) were mixed in N,N-dimethylacetamide (4 kg). The suspension was stirred and heated at 90-95° C. The solution obtained was heated at 90-95° C. for 1 h then N,N-dimethylacetamide (about 3 kg) was distilled under vacuum and brought to a water content lower than 0.5%, assessed by Karl Fischer titration. At this point the formation of intermediate (I) was complete (assessed by $^1$H-NMR). The residue was cooled to 30-35° C. and, under nitrogen atmosphere, (S)-2-(acetyloxy)propanoyl chloride (380 g; 2.52 mol) was slowly added. The mixture was stirred for 18 h at room temperature and under nitrogen atmosphere then water was added to obtain a diluted solution, suitable for the chromatographic purification. After 1 h of stirring the solution was loaded onto a column of Amberlite® IRA743 (17 L) (Dow Chemical Company) and eluted with water (3 bed volumes). The solution was loaded onto a column of Relite® 3ASFB (anionic resin; 4 L) and the eluate was discharged. The Relite 3ASFB column was then sequentially eluted with 2 bed volumes of an aqueous acidic solution (diluted hydrochloric acid), and washed with 3-4 BV (bed volumes) of water, quantitatively recovering the substrate. The obtained solution was neutralized to pH 7, concentrated by vacuum distillation over 2 hours. The solution was loaded onto a column of Amberlite® XAD 1600 (3.6 L) (Dow Chemical Company) and eluted with 4 BV of highly diluted sodium hydroxide solution. The solution was loaded onto two ion exchange resin columns (cationic Dowex® C350, 4.7 L; anionic Relite® MG1/P, 2 L, Dow Chemical Company). The eluate was concentrated and the solid residue was crystallized from 2-butanol to afford Iopamidol (II) (904 g; 1.16 mol) as a pure white solid with a yield of 82%.

The $^1$H-NMR, $^{13}$C-NMR, IR and MS are consistent with the indicated structure.

Phenylboronic acid was recovered with a >90% yield.

An identical procedure was employed with n-butylboronic acid (X=n-Bu) and Iopamidol (II) was recovered with an 80% yield.

Example 2: Preparation of Iopamidol (II) Starting from Compound (IV) and Using a Boronic Acid Referring to Scheme 3, 5-Amino-N,N'-bis[2-hydroxy-1-(hydroxymethyl)ethyl]-2,4,6-triiodo-1,3-benzenecarboxamide (IV) (1 kg; 1.42 mol) and phenylboronic acid (X=Ph) (363 g; 2.98 mol) were mixed in N,N-dimethylacetamide (4 kg). The suspension was stirred and heated at 90-95° C. The solution obtained was heated at 90-95° C. for 1 h then N,N-dimethylacetamide (about 3 kg) was distilled under vacuum. The residue should have water content lower than 0.5%, assessed by Karl Fischer titration. At this point the formation of intermediate (I) was complete, as determined by $^1$H-NMR on an aliquot of the reaction mixture, dried and the residue treated as described below. The residue was cooled to 30-35° C. and, under nitrogen atmosphere, (S)-2-(acetyloxy)propanoyl chloride (384 g; 2.55 mol) was slowly added. The mixture was stirred for 18 h at room temperature and under nitrogen atmosphere then water (9 kg) was added. After 1 h of stirring the solution was loaded onto a column of Relite MG1/P (2.2 L) and eluted with water (15 L). The solution was extracted with 4-methyl-2-pentanone (3×4 L) and the aqueous phase was loaded onto a Relite 3ASFB column for the hydrolysis, sequentially eluted with 2 bed volumes of an aqueous acidic solution (diluted hydrochloric acid), and washed with 3-4 bed volumes of water, quantitatively recovering the substrate. The obtained solution was neutralized to pH 7, concentrated by vacuum distillation over 2 hours. The solution was loaded onto a column of Amberlite® XAD 1600 (3.6 L) and eluted with 4 BV of highly diluted sodium hydroxide solution. The solution was loaded onto two ion exchange resin columns (cationic Dowex® C350, 4.7 L; anionic Relite® MG1/P, 2 L). The eluate was concentrated and the solid residue was crystallized from 2-butanol to afford Iopamidol (II) (959 g; 1.23 mol) as a pure white solid, with a yield of 87%. The $^1$H-NMR, $^{13}$C-NMR, IR and MS are consistent with the indicated structure.

Phenylboronic acid was recovered with a >95% yield. The solvent was distilled off and a concentrated solution is directly reemployed in the synthesis.

Phenylboronic acid was also extracted with 3-pentanone with comparable results.

Procedure for the Isolation of Compound (I):

The protected intermediate (12.4 g) was re-dissolved in dimethylacetamide (10 g) and toluene (100 mL) was added to form a precipitate. The solution was heated at 60° C. over 30 minutes and the precipitate was redissolved; the solution was cooled to 5° C. over 2 h and the obtained solid was filtered off, affording a white solid. The analytical characterization is in agreement with the proposed structure.

Melting point=180-185° C.

$^1$H-NMR (DMSO-$d_6$) (ppm): 4.07 (dd, 1H, 7), 4.31 (dd, 1H, 7), 4.38 (m, 1H, 6), 7.35 (t, 1H, 10), 7.43 (t, 1H, 11), 7.70 (d, 1H, 9), 9.12 (d, 1H, CONH).

$^{13}$C-NMR (DMSO-$d_6$) (ppm): 45.35 (C6), 64.05 (C7), 74.45 (C4), 80.30 (C2), 127.94 (C10), 131.06 (C11), 133.00 (C8), 134.05 (C9), 147.88 (C1), 148.82 (C3), 170.20 (C5).

Example 3: Preparation of Iopamidol (II) Starting from Compound (IV) and Using a Boronic Acid Referring to Scheme 3, 5-Amino-N,N'-bis[2-hydroxy-1-(hydroxymethyl)ethyl]-2,4,6-triiodo-1,3-benzenecarboxamide (V) (1 kg; 1.42 mol) and phenylboronic acid (X=Ph) (360 g; 2.95 mol) were mixed in N,N-dimethylacetamide (0.76 kg) and methyl isobutyl ketone (MIBK) (3.24 kg). The suspension was stirred and heated at 90-95° C., then MIBK/water mixture (2.8 kg) was distilled under vacuum and brought to a water content lower than 0.5%, assessed by Karl Fischer titration, obtaining a clear yellow solution. At this point the formation of intermediate (I) was complete (assessed by $^1$H-NMR). The residue was cooled to 30-35° C. and, under nitrogen atmosphere, (S)-2-(acetyloxy)propanoyl chloride (380 g; 2.52 mol) was slowly added. The mixture was stirred for 18 h at 30-35° C. and under nitrogen atmosphere then diluted NaOH solution was added to neutral pH. Another portion of methyl isobutyl ketone (4-5 kg) was added to the biphasic mixture and phenylboronic acid was extracted. The aqueous phase was loaded onto two ion exchange resin columns (a cationic resin, Dowex® C350, 2 L; an anionic resin Relite® MG1/P, 2.6 L). The columns were eluted with 2 BV of water. The solution obtained was loaded onto Relite 3ASFB column for the hydrolysis: Iopamidol (II) was recovered by elution with 2 BV of an aqueous acidic solution (diluted hydrochloric acid), and washed with 3-4 bed volumes of water. The obtained solution was neutralized to pH 7, concentrated by vacuum distillation over 2 hours. The solution was loaded onto a column of Amberlite® XAD 1600 (3.6 L) and eluted with 4 BV of highly diluted sodium hydroxide solution. The solution was loaded onto two ion exchange resin columns (cationic Dowex® C350, 4.7 L; anionic Relite® MG1/P, 2 L). The eluate was concentrated and the solid residue was crystallized from 2-butanol to afford Iopamidol (II) (992 g; 1.28 mol) as a white solid. Yield 90%.

PBA was recovered with a yield of 95%.

Example 4: Preparation of Iopamidol (II) Starting from Compound (IV) and Using a Boronic Acid The synthesis was carried out essentially as described in Example 3. Briefly, and referring to Scheme 3, 5-Amino-N,N'-bis[2-hydroxy-1-(hydroxymethyl)ethyl]-2,4,6-triiodo-1,3-benzenecarboxamide (V) (1 kg; 1.42 mol) and phenylboronic acid (X=Ph) (360 g; 2.95 mol) were mixed in N,N-dimethylacetamide (0.76 kg) and methyl isobutyl ketone (MIBK) (3.24 kg). The suspension was stirred and heated at 90-95° C., then MIBK/water mixture (2.8 kg) was distilled under vacuum and brought to a water content lower than 0.5%, assessed by Karl Fischer titration, obtaining a clear yellow solution. At this point the formation of intermediate (I) was complete as assessed by $^1$H-NMR. The residue was cooled to 30-35° C. and, under nitrogen atmosphere, (S)-2-(acetyloxy)propanoyl chloride (380 g; 2.52 mol) was slowly added. The mixture was stirred for 18 h at 30-35° C. and under nitrogen atmosphere, then diluted NaOH (9 kg) solution was added to neutral pH. PBA was extracted with three portion of methyl isobutyl ketone (3×3.2 kg). The aqueous phase was loaded onto two ion exchange resin columns (a cationic resin, Dowex® C350, 2 L; an anionic resin Relite® MG1/P, 2.6 L). The columns were eluted with water. The solution obtained was loaded onto Relite 3ASFB column for the hydrolysis: Iopamidol (II) was recovered by elution with an aqueous acidic solution (diluted hydrochloric acid), and washed with water. The obtained solution was loaded onto a column of Relite® MG1/P (1.8 L), Amberlite® XAD 1600 (3.6 L) and cationic Dowex® C350 (0.2 L), and eluted with 4 BV of highly diluted sodium hydroxide solution. The eluate was concentrated and the solid residue was crystallized from 2-butanol to afford Iopamidol (II) (1003 g; 1.29 mol) as a white solid. Yield 91%.

PBA was recovered with a yield of 95%.

Example 5: Preparation of Iopamidol (II) Starting from Compound (IV) and Using a Recycled Phenyl Boronic Acid (PBA)

It has been tested whether the recovered phenyl boronic acid could be re-used by direct addition to the reaction mixture.

Referring to Scheme 3, the organic phase (MIBK containing phenyl boronic acid), obtained from phenylboronic acid extraction and recovered from the reaction mixture obtained in example 4, was used to perform a synthesis of a new batch of Iopamidol. DMAC (0.6 kg) was first added to the organic mixture and the solution was distilled under vacuum at <40° C. concentrating the PBA, to reach a suitable concentration. Subsequently the organic solution, containing 95% of the required recovered phenyl boronic acid, was mixed with -Amino-N,N'-bis[2-hydroxy-1-(hydroxymethyl)ethyl]-2,4,6-triiodo-1,3-benzenecarboxamide (V) (1 kg; 1.42 mol) and fresh phenylboronic acid (X=Ph) (18 g; 0.15 mol), corresponding to about 5% of the total amount required, was added. The suspension was stirred and heated at 90-95° C., and the reaction was continued as described in Example 4, affording Iopamidol yields comparable to that obtained with solid (fresh) PBA.

Example 6. Preparation of Iopamidol (II) Starting from Compound (IV) with Phenylboronic Acid (PBA) in DMAC and a Co-Solvent. Recovery of PBA The synthesis was carried out substantially as described in Example 4, but using reduced volumes.

Briefly: 5-Amino-N,N'-bis[2-hydroxy-1-(hydroxymethyl)ethyl]-2,4,6-triiodo-1,3-benzenecarboxamide (V) (1 kg; 1.42 mol) and phenylboronic acid (X=Ph) (360 g; 2.95 mol) were mixed in N,N-dimethylacetamide (0.76 kg) and methyl isobutyl ketone (MIBK) (3.24 kg). The suspension was stirred and heated at 90-95° C., then MIBK/water mixture (2.8 kg) was distilled under vacuum and brought to a water content lower than 0.5%, assessed by Karl Fischer titration, obtaining a clear yellow solution. At this point the formation of intermediate (I) was complete as assessed by 1H-NMR. The residue was cooled to 30-35° C. and, under nitrogen atmosphere, (S)-2-(acetyloxy)propanoyl chloride (380 g; 2.52 mol) was slowly added. The mixture was stirred for 18 h at 30-35° C. and under nitrogen atmosphere, then NaOH (2.7 kg) was added to neutral pH. Another portion of methyl isobutyl ketone (2 kg) was added to the biphasic mixture and phenylboronic acid was extracted. The organic phase was washed with water (0.9 kg) and the aqueous phases were collected and extracted with two other portions of MIBK (2 kg). Less than 0.8% of Acetyl-Iopamidol passed into the organic phase. The aqueous phase was loaded into two ion resin columns and the work up was continued as described above.

The organic phase (MIBK containing phenyl boronic acid), obtained from phenylboronic acid extraction and recovered from the reaction mixture, was used to perform a synthesis of a new batch of Iopamidol, essentially as described in Example 5. Briefly, DMAC (0.6 kg) was first added to the organic mixture and the solution was distilled under vacuum at <40° C. removing 2-2.3 kg of MIBK in order to have a final amount of 3.65 Kg of MIBK. Subsequently the organic solution, containing 95% of the required recovered phenyl boronic acid, was mixed with -Amino-N, N'-bis[2-hydroxy-1-(hydroxymethyl)ethyl]-2,4,6-triiodo-1, 3-benzenecarboxamide (V) (1 kg; 1.42 mol) and fresh phenylboronic acid (X=Ph) (18 g; 0.15 mol), corresponding to about 5% of the total amount required, was added. The suspension was stirred and heated at 90-95° C., and the reaction was continued as previously described, to Iopamidol.

Example 7. Preparation of Iopamidol (II) Starting from Compound (IV) with Phenylboronic Acid (PBA) In DMAC and a Co-Solvent. Recovery of PBA with 2-Pentanone The process was carried out substantially as described in Example 4 using 2-pentanone instead of MIBK. In brief: 5-Amino-N,N'-bis[2-hydroxy-1-(hydroxymethyl)ethyl]-2,4, 6-triiodo-1,3-benzenecarboxamide (V) (1 kg; 1.42 mol) and phenylboronic acid (X=Ph) (360 g; 2.95 mol) were mixed in N,N-dimethylacetamide (0.76 kg) and 2-pentanone (3.24 kg). The suspension was stirred and heated at 90-95° C., then 2-pentanone/water mixture (2.8 kg) was distilled under light vacuum and brought to a water content lower than 0.5%, assessed by Karl Fischer titration, obtaining a clear yellow solution. At this point the formation of intermediate (I) was complete as assessed by 1H-NMR. The residue was cooled to 30-35° C. and, under nitrogen atmosphere, (S)-2-(acetyloxy)propanoyl chloride (380 g; 2.52 mol) was slowly added. The mixture was stirred for 18 h at 30-35° C. and under nitrogen atmosphere, then NaOH solution (4.4 kg) was added to neutral pH. Another portion of 2-pentanone (2.4 kg) was added to the biphasic mixture and phenylboronic acid was extracted. The extraction was repeated 2 more times with 2-pentanone (1.6 kg×2). A quantitative recovery of PBA was achieved but ca. 4% of Acetyl-Iopamidol was found into the organic phase.

The procedure was repeated by washing the organic phase (2-pentanone) with water thus recovering more product and affording an equivalent PBA recovery.

Example 8. Recovery of PBA by Using Diluted NaOH Solution and Higher Solvent Volumes The process was carried out substantially as described in Examples 6 and 7 but using higher volumes of a more diluted NaOH solution. In this case, the aqueous phase was re-extracted with about twice the volume of solvent to achieve the same recovery of Acetyl-Iopamidol and PBA.

A similar workout was carried out with 3-pentanone, 2-pentanone, methyl isopropyl ketone, methyl-isopenthyl ketone and cyclopentyl methyl ether, that afforded comparable Iopamidol synthetic yields, as well as both Iopamidol and PBA recovery yields.

Example 9. Preparation of Iopamidol (II) Starting from Compound (IV) and Using p-Tolylboronic Acid Referring to Scheme 3, 5-Amino-N,N'-bis[2-hydroxy-1-(hydroxymethyl)ethyl]-2,4,6-triiodo-1,3-benzenecarboxamide (V) (1 kg; 1.42 mol) and p-tolylboronic acid (405 g; 2.98 mol) were mixed in N,N-dimethylacetamide (0.75 kg) and methyl isobutyl ketone (MIBK) (3.25 kg). The suspension was stirred and heated at 90-95° C., then MIBK/water mixture (2.8 kg) was distilled under vacuum and brought to a water content lower than 0.5%, assessed by Karl Fischer titration, obtaining a clear yellow solution. At this point the formation of intermediate (I) was complete as assessed by 1H-NMR. The residue was cooled to 30-35° C. and, under nitrogen atmosphere, (S)-2-(acetyloxy)propanoyl chloride (380 g; 2.52 mol) was slowly added. The mixture was stirred for 18 h at 30-35° C. and under nitrogen atmosphere, then diluted NaOH solution was added to neutral pH. Another portion of methyl isobutyl ketone (4 kg) was added to the biphasic mixture and p-tolylboronic acid was extracted. The aqueous phase was loaded onto two ion exchange resin columns (a cationic resin, Dowex® C350, 2 L; an anionic resin Relite® MG1/P, 2.6 L) and the work-up was continued as described in Example 4 to afford Iopamidol (11) (992 g; 1.28 mol) as a white solid. Yield 90%

Example 10: Preparation of Iopamidol (II) Starting from Compound (IV) and Using Butylboronic Acid Referring to Scheme 3, 5-Amino-N,N'-bis[2-hydroxy-1-(hydroxymethyl)ethyl]-2,4,6-triiodo-1,3-benzenecarboxamide (V) (1 kg; 1.42 mol) and butylboronic acid (303.6 g; 2.98 mol) were mixed in N,N-dimethylacetamide (4.0 kg). The suspension was stirred and heated at 90-95° C., then DMA/water mixture (2.8 kg) was distilled under vacuum and brought to a water content lower than 0.5%, assessed by Karl Fischer titration, obtaining a clear yellow solution. At this point the formation of intermediate (I) was complete as assessed by 1H-NMR. The residue was cooled to 25° C. and, under nitrogen atmosphere, (S)-2-(acetyloxy)propanoyl chloride (380 g; 2.52 mol) was slowly added. The mixture was stirred for 18 h at RT and under nitrogen atmosphere, then diluted NaOH solution was added to neutral pH. A portion of methyl isobutyl ketone (5 kg) was added to the biphasic mixture and butylboronic acid was extracted. The aqueous phase was loaded onto two ion exchange resin columns (a cationic resin, Dowex® C350, 2 L; an anionic resin Relite® MG1/P, 2.6 L) and the work-up was continued as described in Example 4 to afford Iopamidol (II) (992 g; 1.28 mol) as a white solid.
Yield 90%.

Example 11: Preparation of Iopamidol (II) Starting from Compound (IV) and Using a Boroxine Referring to Scheme 3, 5-Amino-N,N'-bis[2-hydroxy-1-(hydroxymethyl)ethyl]-2,4,6-triiodo-1,3-benzenecarboxamide (V) (255 g; 0.362 mol) and triphenylboroxine (Compound (III), $R_3$=Ph) (82.3 g; 0.264 mol) were mixed in N,N-dimethylacetamide (1 kg). The suspension was stirred and heated at 90-95° C. The solution obtained was heated at 90-95° C. for 1 h then N,N-dimethylacetamide (about 700 g) was distilled under vacuum. The residue should have water content lower than 0.5%, assessed by Karl Fischer titration. At this point the formation of intermediate (I) was complete (assessed by $^1$H-NMR). The residue was cooled to 30-35° C. and, under nitrogen atmosphere, (S)-2-(acetyloxy)propanoyl chloride (98 g; 0.651 mol) was slowly added. The mixture was stirred for 18 h at room temperature and under nitrogen atmosphere then water (190 g) was added. After 1 h of stirring the solution was purified by elution on a series of columns as described in Example 4 to afford Iopamidol (II) (219 g; 0.282 mol) as a white solid.

Yield: 78%. The H-NMR, $^{13}$C-NMR, IR and MS are consistent with the indicated structure.

An identical procedure was employed with trimethylboroxine (III) ($R_3$=Me); Iopamidol (II) yield was 75%.

Example 12: Preparation of Iopamidol (II) Starting from Compound (IV) and Using a Boric Acid Ester Referring to Scheme 3, 5-Amino-N,N'-bis[2-hydroxy-1-(hydroxymethyl)ethyl]-2,4,6-triiodo-1,3-benzenecarboxamide (IV) (200 g; 0.284 mol) in N,N-dimethylacetamide (800 g) was heated at 60° C. obtaining a solution then tri-n-butyl borate (X=$OR_2$, $R_2$=n-Bu) (137.2 g; 0.596 mol) was added. The solution was stirred and heated at 105° C. for 2 h then N,N-dimethylacetamide and n-butanol were distilled under vacuum collecting about 730 g of distillate. More N,N-dimethylacetamide (95 g) was added to the reaction mixture and distilled under vacuum. At this point the formation of intermediate (I) was complete (assessed by $^1$H-NMR). The residue was cooled to room temperature and, under nitrogen atmosphere, (S)-2-(acetyloxy)propanoyl chloride (85.5 g; 0.568 mol) was slowly added. The mixture was stirred for 18 h at room temperature and under nitrogen atmosphere then water (1.5 kg) was added, deprotecting the hydroxyl groups and obtaining a diluted solution suitable for the chromatographic purification. After 1 h of stirring the solution was loaded onto a column of XAD® 1600 (4 L), the resin was washed with water (3 BV) and the eluate containing boric acid, N,N-dimethylacetamide and butanol was loaded onto a column of IRA743 (4.1 L) for DMAC, butanol and boric acid recovery. Acetyl Iopamidol was eluted from XAD 1600 with NaOH (0.20% w/w; 5 BV), concentrated under vacuum to a final volume of 2 L and hydrolyzed in batch with NaOH at pH=12 at 35° C. over 20-24 hours. The solution was loaded onto two ion exchange resins (a cationic Amberjet® 1200, 0.9 L; an anionic Relite® MG1, 0.8 L). The eluate was concentrated and the solid residue was crystallized from 2-butanol to afford Iopamidol (II) (159 g; 0.205 mol) as a white solid.

Yield: 72%. The $^1$H-NMR, $^{13}$C-NMR, IR and MS are consistent with the indicated structure.

An identical procedure was employed with triethyl borate and tri-n-propyl borate.

Example 13: Preparation of Iopamidol (II) Starting from Compound (IV) and Using a Boric Acid and Alcohol Referring to Scheme 3, 5-Amino-N,N'-bis[2-hydroxy-1-(hydroxymethyl)ethyl]-2,4,6-triiodo-1,3-benzenecarboxamide (IV) (200 g; 0.284 mol), n-BuOH (600 g, 8.10 mol) and boric acid (36.8 g, 0.60 mol) were suspended in N,N-dimethylacetamide (720 g) and heated at 60° C., obtaining an homogeneous solution. The solution was stirred and heated at 90° C. for 1 h then N,N-dimethylacetamide and n-butanol were distilled under vacuum over 4 h, collecting about 1.1 kg of distillate. At this point the formation of intermediate (I) was complete (assessed by $^1$H-NMR). The residue was cooled to room temperature and, under nitrogen atmosphere, (S)-2-(acetyloxy)propanoyl chloride (85.28 g; 0.57 mol) was slowly added. The mixture was stirred over 18 h at room temperature under nitrogen atmosphere, then water (1.5 kg) was added. After 1 h of stirring the solution was loaded onto a column of XAD® 1600 (4 L), the resin was washed with water (3 BV) and the eluate containing boric acid, DMAC and n-BuOH was loaded onto a column of IRA743 (4.1 L) for DMAC, n-BuOH and boric acid recovery. Acetyl Iopamidol was eluted from XAD 1600 with NaOH (0.20% w/w; 5 bed volumes), concentrated under vacuum to a final volume of 2 L and hydrolyzed in batch with NaOH at pH=12 and at 35° C. The solution was loaded onto two ion exchange resins (a cationic Amberjet® 1200, 0.9 L; an anionic Relite® MG1, 0.8 L). The eluate was concentrated and the solid residue was crystallized from 2-butanol to afford Iopamidol (II) (170 g; 0.218 mol) as a white solid. Yield: 77%.

Example 14: Procedure: One Pot Synthesis Starting from 5-Nitroisophthalic Acid to Compound (V)

Referring to Scheme 6, 5-nitro isophthalic acid (NIPA; 100 g; 0.47 mol) was dissolved in butanol (600 g), in the presence of a catalytic amount of monohydrated p-toluenesulphonic acid (9.01 g; 0.047 mol). The mixture was heated at 125° C. and the water was azeotropically removed by distillation. The intermediate (VI) was obtained with a quantitative conversion (>98%). The homogeneous solution was hydrogenated without isolation in presence of 5% Pd/C (3.0 g) as a catalyst. The obtained suspension was maintained under mechanical stirring and purged with nitrogen washings, at the end of which the hydrogenation reaction was carried out at a temperature comprised between 50 and 70° C. The reaction was complete in 4-8 hours (132.76 g; 0.453 mol). A nitrogen flow was passed through the reaction vessel to wash out any hydrogen gas, the catalyst was filtered off and the obtained solution transferred to a new reactor.

Concerning the amidation, the reaction was carried out by two alternatives methods.
i) Amidation Employing Methanol as a Co-Solvent:
Serinol in slight excess (94.84 g; 1.04 mol) was loaded to the hydrogenated mixture, containing 132.76 g of (VII). The solution was concentrated, removing the water generated in the previous step and most of the butanol.

The mixture was cooled, methanol (524 g) was added and the temperature was increased to 55-60° C. A solution of sodium methylate (21.19 g; 0.118 mol) in methanol was added dropwise and kept to this temperature until complete conversion (7-10 hours). The mixture was cooled to 15° C. and kept for 3 h, and then the solid was filtered off, affording a white solid (V), that was washed with methanol. The solid obtained was directly redissolved in water and transferred to a reactor for the next iodination reaction. Yield based on a dried solid=95%
ii) Neat Amidation, with an Excess of Serinol:
The hydrogenated mixture, containing (VII) (132.76 g; 0.45 mol) was cooled to room temperature and an excess of serinol (247.40 g; 2.72 mol) was added. The solution was concentrated, azeotropically removing the mixture water/ butanol at 100° C. under vacuum. The mixture was heated at 125° C. over a period of 4-6 hours, then cooled at 70-80° C. Water (929.3 g) was loaded into the reactor. The diluted solution thus obtained was loaded onto a series of two columns, the first one was a weak acidic resin (carboxylic, 700 mL) to selectively recover and recycle serinol, the second one was an anionic resin (tertiary amine, 50 mL) to purify the (V) solution.

Procedure for Iodination: with (V) coming from cosolvent procedure:

ia) The wet solid (735 g; 2.05 mol) was redissolved in water (7 L), the residual methanol was distilled off, heating at 70-75° C., then the solution was heated at 70-90° C. and sulfuric acid (106 g; 1.03 mol) was loaded. ICl (1919 g; 6.65 mol) was added dropwise over 1.5 h. (IV) started to precipitate and the suspension was heated over 6-8 h. The suspension was cooled to room temperature and the precipitate filtered off, affording a white solid. Yield=92% iia) Iodination with (V) Coming from Neat Procedure:

The solution coming from the amidation was concentrated, heated at 70-90° C. and sulfuric acid was loaded. The procedure was as reported above.

The synthesis of Iopamidol (II) was then carried out according to scheme 3 or to any one of the preceding Examples.

The invention claimed is:

1. A process for recovery of a boronic acid of formula $R_3$—$B(OH)_2$, wherein $R_3$ is selected from the group consisting of $C_1$-$C_6$ linear or branched alkyl, $C_3$-$C_6$ cycloalkyl, and $C_6$ aryl, optionally substituted with a group selected from the group consisting of methyl, ethyl, n-propyl, i-propyl, n-butyl, sec-butyl, t-butyl, and phenyl, from an aqueous mixture optionally comprising a polar solvent, said process comprising the following steps:

admixing an aqueous mixture comprising a boronic acid of formula $R_3$—$B(OH)_2$, wherein $R_3$ is as defined above, with a water-immiscible organic solvent in a weight ratio between the boronic acid and the water-immiscible organic solvent from 1:10 to 1:20, wherein the organic water-immiscible solvent is selected from the group consisting of 4-methyl-2-pentanone (MIBK), 3-pentanone, 2-pentanone, dibutyl ether, 2-methyl-tetrahydrofurane, cyclopentylmethyl ether, methyl isopropyl ketone, and methyl isopentyl ketone, and wherein the aqueous mixture optionally comprises a polar solvent, adding an aqueous solution to a final pH from 6 to 7, and partitioning the boronic acid into the organic water-immiscible phase and recovery of the organic water-immiscible phase.

2. The process according to claim 1, wherein the boronic acid of Formula $R_3$—$B(OH)_2$ is used for diol protection or is formed after hydrolysis of a diol protection group.

3. The process according to claim 1, wherein the weight ratio between the boronic acid and the water-immiscible organic solvent is from 1:13 to 1:16 (w/w).

4. The process according to claim 1, wherein $R_3$ is selected from the group consisting of methyl, butyl, and phenyl, optionally substituted with methyl.

5. The process according to claim 1, wherein the process is carried out in a batch or in a continuous mode.

6. The process according to claim 1, wherein the process is carried out in a batch mode.

7. The process according to claim 1, wherein the process is carried out in a continuous mode.

* * * * *